(12) United States Patent
Lancesseur et al.

(10) Patent No.: US 7,628,292 B2
(45) Date of Patent: Dec. 8, 2009

(54) DEVICE FOR DISPENSING OBLONG OBJECTS, COMPRISING ONE MAIN OPENING AND AT LEAST ONE OTHER ELONGATED OPENING

(75) Inventors: Didier Lancesseur, Boulogne (FR); Roger Nobilet, Torcy (FR)

(73) Assignee: Airsec S.A., Choisy le Roi ( * ) Notice: Subject to any disclaimer, the term of this patent is extended or adjusted under 35 U.S.C. 154(b) by 404 days.

(21) Appl. No.: 10/547,483

(22) PCT Filed: Mar. 3, 2004

(86) PCT No.: PCT/FR2004/000487

§ 371 (c)(1),
(2), (4) Date: Sep. 13, 2006

(87) PCT Pub. No.: WO2004/080366

PCT Pub. Date: Sep. 23, 2004

(65) Prior Publication Data

US 2007/0034630 A1 Feb. 15, 2007

(30) Foreign Application Priority Data

Mar. 3, 2003 (FR) .................. 03 02728
Mar. 3, 2003 (FR) .................. 03 02729

(51) Int. Cl.
*B65H 3/00* (2006.01)
(52) U.S. Cl. ............... 221/267; 221/309; 221/310
(58) Field of Classification Search ........... 221/267, 221/309, 310
See application file for complete search history.

(56) References Cited

U.S. PATENT DOCUMENTS

| 2,173,046 A | | 9/1939 | Smith |
| 2,918,167 A | | 12/1959 | Lowen |
| 3,435,988 A | * | 4/1969 | Pfund et al. .................. 221/310 |
| 3,517,855 A | | 6/1970 | Hillis |
| 3,581,934 A | * | 6/1971 | Sciascia ...................... 221/304 |
| 4,228,920 A | | 10/1980 | Burton |
| 4,240,564 A | | 12/1980 | Pritchard |
| 4,266,690 A | * | 5/1981 | Holmes et al. ............... 221/254 |
| 4,782,981 A | | 11/1988 | Schuster |
| 5,505,308 A | | 4/1996 | Eikmeier et al. |
| 5,736,616 A | | 4/1998 | Ching et al. |
| 5,788,064 A | | 8/1998 | Sacherer et al. |

(Continued)

FOREIGN PATENT DOCUMENTS

DE 8437898 7/1985

(Continued)

*Primary Examiner*—Gene Crawford
*Assistant Examiner*—Timothy R Waggoner
(74) *Attorney, Agent, or Firm*—Scott R. Cox

(57) ABSTRACT

A device for dispensing oblong objects comprising: (i) a main dispensing opening for allowing the objects to be dispensed to pass therethrough one by one; (ii) at least one other opening of elongate shape, one of whose sides opens into the main dispensing opening, the elongate opening having an opening width equal to or greater than a minimum thickness of the object to be dispensed; and (iii) guide surfaces for guiding the objects to be dispensed. The guide surfaces lie along front sides of the elongate opening and face the objects to be dispensed, so as to collect and guide the objects toward at least one of the elongate openings.

27 Claims, 2 Drawing Sheets

U.S. PATENT DOCUMENTS

| | | |
|---|---|---|
| 6,334,974 B1 | 1/2002 | Chen |
| 6,497,845 B1 | 12/2002 | Sacherer |
| 2003/0010668 A1 | 1/2003 | Taskis et al. |
| 2006/0169603 A1 | 8/2006 | Lancesseur et al. |

FOREIGN PATENT DOCUMENTS

| | | |
|---|---|---|
| FR | 2624106 | 6/1989 |
| FR | 2709475 A3 | 3/1995 |
| GB | 539891 | 9/1941 |
| GB | 1074165 | 6/1967 |
| GB | 2210603 A | 6/1989 |
| JP | 09315455 | 12/1997 |
| JP | 2003 118758 | 4/2003 |
| WO | WO9409084 A1 | 4/1994 |
| WO | WO9528338 A1 | 10/1995 |
| WO | WO9851758 A1 | 11/1998 |
| WO | WO9948963 A2 | 9/1999 |
| WO | WO2004024593 A1 | 3/2004 |
| WO | WO2006040019 A1 | 4/2006 |

* cited by examiner

Seen from above

A-A

B-B

DEVICE FOR DISPENSING OBLONG OBJECTS, COMPRISING ONE MAIN OPENING AND AT LEAST ONE OTHER ELONGATED OPENING

CROSS REFERENCE TO RELATED APPLICATIONS

This application is a §371 national stage application of International Application No. PCT/FR04/000487 filed Mar. 3, 2004 which claims priority to French Application Nos. 03/02728 and 03/02729, both of which were filed on Mar. 3, 2003.

BACKGROUND OF THE INVENTION

1. Field of the Invention

The invention relates to a device for dispensing oblong objects, in particular those having a substantially polygonal, circular or elliptical cross section, and to the container equipped with such a dispensing device.

2. Description of Related Art

Many objects having an elongate shape, in particular those having a substantially polygonal, circular or elliptical cross section, are used as consumables. Such objects are, for example, strips, including test strips in the form of rigid bands or lamellae used for example for diagnostic or monitoring purposes in the medical field. Other objects to be dispensed having an oblong shape may also be for example bandages, or food products such as strips of chewing gum, toothpicks, orange sticks, chopsticks, or the like.

For obvious reasons, particularly hygiene reasons, but also to avoid any degradation and thus improve the preservation time of the objects, they are protected from external contamination and/or from physico-chemical attack resulting from the relative humidity level, or light, in particular UV radiation and other chemical substances, or else from mechanical degradation.

Also for hygiene, preservation and protection reasons, many dispensing devices have been designed to allow the oblong objects to be dispensed one by one, so as to dispense the precise number of objects required and thus to avoid any contamination due to unintentional removal of an object.

Such object-dispensing devices must be simple, inexpensive to produce and easy to use.

Many devices for dispensing substantially flat objects have been described in the technical literature, in particular in that formed by published patent applications and/or patents.

In a first document of the prior art (U.S. Pat. No. 5,505,308), a device for storing moisture-sensitive test strips is described.

The storage device appears to be formed from a container, which includes a desiccant, and from a lid assembled so as to be able to be disengaged from the opening of said container by a translational movement followed by a rotational movement.

When in use, the lid is disengaged from the opening of the container by a translational movement in the direction parallel to the direction of extraction of the test strips, and then by a rotational movement, so as to allow access to the test strips. Said test strips are themselves partly expelled from the container by means of a spring, so as to allow the user to grip them.

This dispensing device has many technical disadvantages such as, for example, the fact that several strips are pushed out of the container simultaneously, consequently increasing the risk of contamination and/or mechanical deterioration of the test strips not extracted each time the container is opened. In addition, when a test strip is gripped, the user's fingers or the tools for gripping the strips come into contact with several of these strips, with the risk of degrading or contaminating, by external pollution, the active surfaces of said strips.

This device is also complex and relatively expensive to produce as it requires the use of a device for extracting the test strips using a spring and a lid of complex kinematics. Another drawback of this system is that it generally requires, when opening it, the use of both hands, making it relatively awkward.

Another document (U.S. Pat. No. 5,788,064) describes a device for dispensing test strips that includes a desiccant and a lid which, once closed, prevents the ingress of moisture. Unlike other devices, in particular the one mentioned above, this device does not have a means for dispensing the test strips that is designed to push on them, the dispensing taking place by inverting the container. At the moment when it is opened, the lid of the container swings away, by rotating about an axis perpendicular to the strip dispensing axis, so as to be partly clear of the opening of the container and to allow the strips to be removed. The strips leaving the container are deflected toward a stop by means of a surface of the lid facing the opening, thus preventing the strips from falling out.

In the same way as in the case of the device described in U.S. Pat. No. 5,505,308, the above dispensing device has disadvantages owing to the fact that, when opening the container, several strips may be extracted simultaneously, without being able to check the number thereof, thus risking unintentional deterioration of certain test strips put back into the container. Another drawback of this device is due to the fact that the opening for extracting the strips is of large size, thus increasing the risk of contaminating the inside of the container.

None of the devices of the prior art gives satisfactory results, as these devices do not allow the number of objects or strips extracted from the container to be checked. Furthermore, such devices do not make it possible to guarantee no contamination or soiling of the strips inadvertently extracted and then put back into the container, as they are not used, being redundant, thus degrading the quality with which the strips are stored. Furthermore, the dispensing devices of the prior art are often made up from many mechanical parts, which increases both their production cost and creates difficulties in producing and handling these devices.

SUMMARY OF THE INVENTION

A problem posed is to produce a device for dispensing oblong objects, in particular those having a substantially polygonal, circular or elliptical cross section, such as for example rigid bands or strips, which not only allows these objects to be dispensed one by one but also completely or partly solves the abovementioned drawbacks.

Only one selected and dispensed object has to come into contact with the environment external to the container, the other objects remaining protected inside the container.

Such a dispensing device has to be suitable for being operated with just one hand, thus making it easier to manipulate, the other hand being free to grip the object dispensed.

Consequently, the invention relates firstly to a device for dispensing oblong objects, in particular those having a substantially polygonal, circular or elliptical cross section, allowing said objects to be dispensed one by one, characterized in that it includes:

a main dispensing opening for allowing the objects to be dispensed to pass through it one by one;

at least one other opening of elongate shape, one of whose sides opens into the main dispensing opening, the elongate opening having an opening width close, and preferably equal to or greater than, the minimum thickness of the object to be dispensed; and guide surfaces for guiding the objects to be dispensed, said surfaces lying along the front sides of the one or more elongate openings and facing the objects to be dispensed, so as to collect and guide said objects to be dispensed toward at least one of the elongate openings.

The invention also relates to a container for containing the oblong objects to be dispensed, the dispensing device being mounted at one of the ends of said container.

DETAILED DESCRIPTION OF A PREFERRED EMBODIMENT

Figures 1, 2:
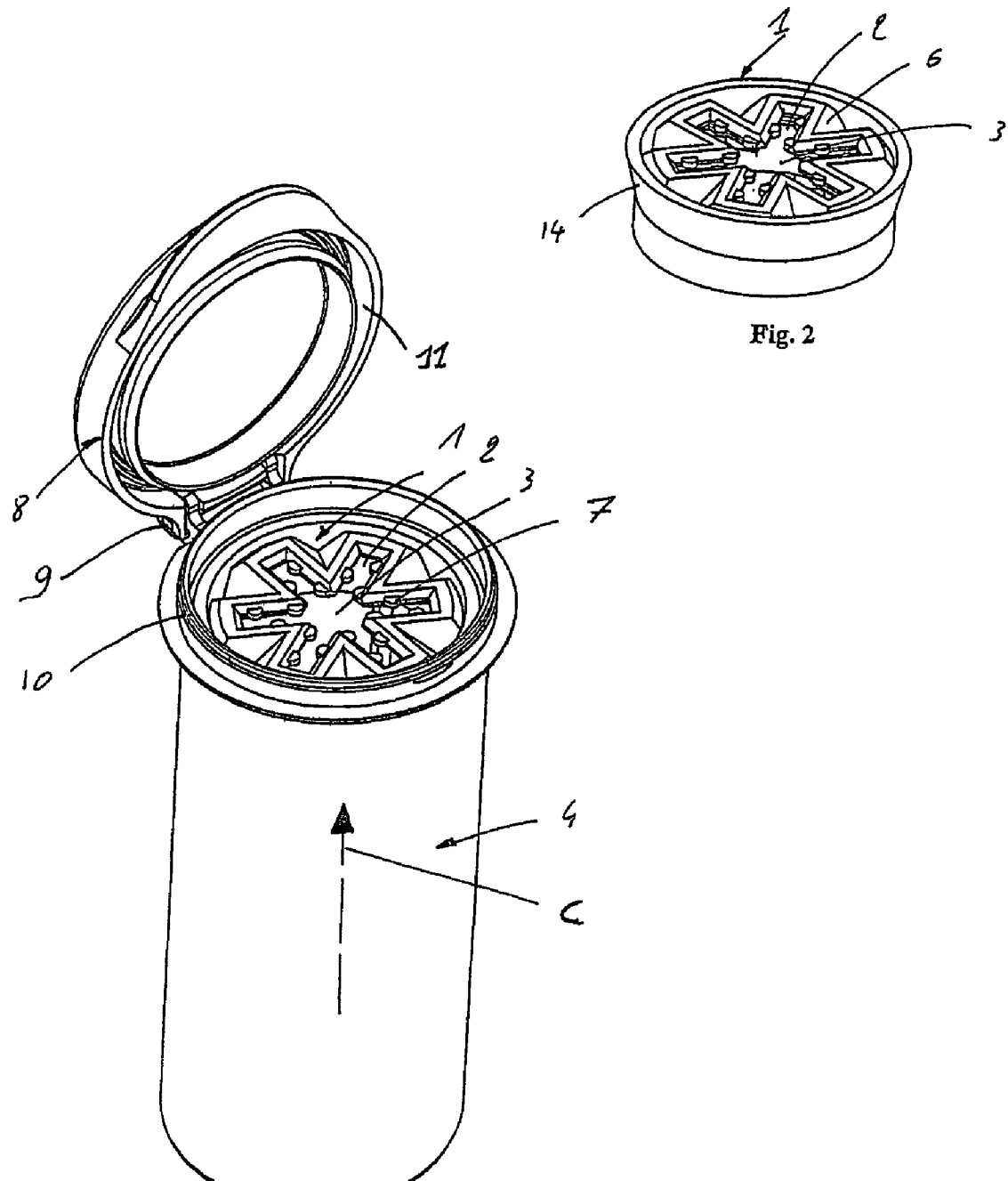
FIG. 1 shows a perspective view of a dispensing container fitted with its dispensing device.
FIG. 2 shows a perspective view of just a dispensing device.

Thus, such a device associated with a container is used to separate and dispense, one by one, a stock of objects to be dispensed, which are being stored ready to be used and protected from the external environment.

When the dispensing operation is required, the user reverses the orientation or configuration of the dispensing device by upturning it, in such a way that the stock of objects to be dispensed now lies above said dispensing device in contact with its front surface.

By inverting the orientation of the device, and consequently through the action of gravity, the objects to be dispensed come in succession into contact:

firstly, with the guide surfaces placed on either side of the elongate openings. Each guide surface has the function of positioning the objects to be dispensed so that one of the ends of the oblong objects to be dispensed is brought substantially parallel to the elongate opening located near the guide surface;

then with the one or more elongate openings, which may have the appearance of a slot, made through the dispensing device.

The objects to be dispensed, undergoing the movement caused by inversion and by the shock of contact between the objects to be dispensed and the guide surfaces on the front face of the dispensing device are collected and directed toward at least one of the elongate openings, and slide along these elongate openings toward the main dispensing opening.

The main dispensing opening may be of polygonal, circular or oval shape. This opening has dimensions that allow only one object to pass through it at a time. Thus, if the main dispensing opening is circular, its diameter is generally close to the width or diameter of the object to be dispensed. Consequently, whatever the number of elongate openings that open into the main dispensing opening, only a single object will be dispensed at a time.

The elongate openings have a length at least equal to twice the width of the objects to be dispensed and preferably at least equal to three times the width of said objects to be dispensed. The elongate openings have a width close to the minimum thickness of the object to be dispensed, in such a way that the object is positioned in an elongate opening and, preferably, is lightly held in the latter, while sliding toward the main dispensing opening.

The function of collecting the objects to be dispensed is consequently accomplished by means of the elongate opening or openings, allowing one or more objects to be guided toward the main dispensing opening.

The function of selecting the object to be dispensed is consequently accomplished mainly at the main dispensing opening. When several objects to be dispensed are guided by the elongate opening(s) and arrive at the same time in the region of the main dispensing opening, a single object can be selected and dispensed through this main dispensing opening, the other objects remaining blocked inside the container.

In general, the selected object engages in and partly passes through the main dispensing opening and remains slightly gripped therein, in such a way that it cannot fall out of the container. Thus, part of the object thus selected by this device lies outside the container and becomes accessible to the user on the rear surface side of the device, allowing the accessible part of the object to be easily gripped and the object to be completely extracted from the container.

The dispensing of a further object takes place by again inverting or shaking the dispensing device so that it is in a downward orientation such that the stock of objects to be dispensed is in contact with the front surface of the device.

The main dispensing opening is placed at any point on the surface of the dispensing device, and may be placed tangentially to the external perimeter of said device. However, this opening is preferably coaxial with the axis of symmetry of the dispensing device.

Other advantages of the oblong object dispenser according to the invention will become apparent on reading the detailed exemplary embodiment of the invention, with reference to the drawings given by way of illustration.

DETAILED DESCRIPTION OF THE INVENTION

FIG. 1 shows a perspective view of the dispensing device (1), in the form of a disk, placed inside a cylindrical dispensing container (4) that contains the oblong objects (13) to be dispensed. As mentioned above, the oblong objects to be dispensed are, in this particular descriptive case, test strips frequently used in the field of medical diagnostics or chemical analysis.

FIG. 2 shows a detailed perspective view of the disk-shaped dispensing device (1), separated from its container.

This device (1) comprises a main dispensing opening (3), that is preferably but not exclusively circular, into which a series of elongate openings (2) opens, said elongate openings being arranged radially around the axis of the main dispensing opening (3).

Preferably, the elongate openings are distributed uniformly around the axis of symmetry of the main dispensing opening (3) and form, for example, an X, if four elongate openings are used, or a six-pointed star if six elongate openings are distributed around the main dispensing opening (3).

The number of elongate openings (2) that open into the main dispensing opening (3) is not limited. However, it has been found that better dispensing of the objects (13) occurs when six elongate openings are uniformly distributed around the main axis of symmetry of a circular main dispensing opening (3).

In general, the elongate openings (2), made through the dispensing device, are in the form of slots whose sides are approximately parallel to one another, giving the elongate opening a substantially constant width. The longitudinal sides of these slots are spaced apart by a distance substantially equal to slightly less than the thickness of the oblong object to be dispensed, in such a way that the latter can pass completely through the slot only by being mechanically forced through it, by pulling slightly on the part that has emerged from the device when gripping it.

The elongate openings (2) may also be in the form of slots whose width increases slightly in the direction going from the perimeter of the elongate opening toward the main dispensing opening (3). Preferably, the slot of increasing width is formed from two substantially straight longitudinal sides making between them a slightly open angle toward the main dispensing opening, the value of this angle generally lying within the range from 0° to 10°, this value being adjusted according to the type of object dispensed and the materials and the shape of the dispensing device.

By applying a sharp movement to the dispensing device, and consequently to the oblong objects to be dispensed that are placed inside the container, certain objects may be introduced, through the action of their kinetic energy, into the elongate openings in the form of increasingly wide slots. In this case, and again through the action of this same kinetic energy, the objects will naturally slide toward the main dispensing opening, since the closer the object to be dispensed gets to the main dispensing opening the less it will be compressed between the sides of the slot. In certain cases, the objects that are introduced into such slots and have not been dispensed remain blocked at the point where the space between the sides of the slot is substantially equal to the thickness of the object to be dispensed. This increasingly wide slot is therefore advantageous not only for directing the objects toward the main dispensing opening but also, in certain cases for keeping the objects introduced into one of the elongate openings, but not yet dispensed, by being gently held therein or through slight friction.

The elongate openings (2) may have many shapes, but are especially rectangular. Elongate openings may also have at least one of their sides curved, or else both sides curved symmetrically, in such a way that the curved sides form an elongate opening, creating restrictions in portions. It is obvious that many shapes of elongate openings may be used to form such a restriction, without departing from the scope of the invention. The restriction in the elongate opening is generally positioned halfway along the length of the opening, so as to slightly and locally grip one of the oblong objects to be dispensed.

Figure 3:
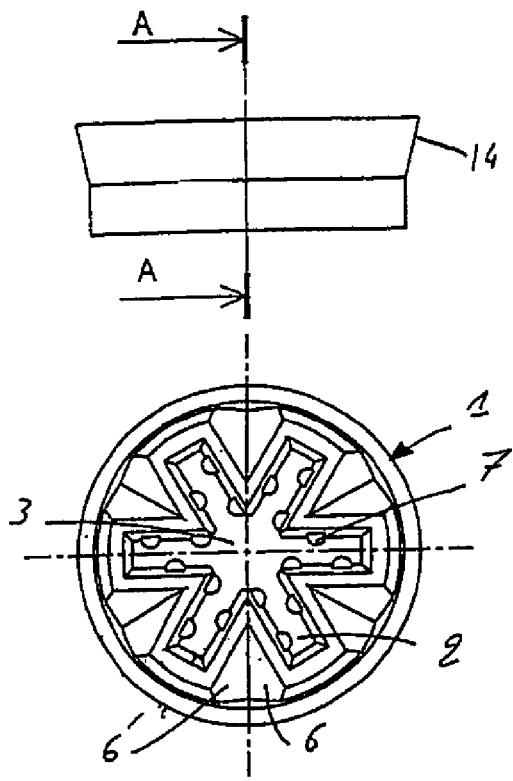
FIG. 3 shows a dispensing device seen from above.

Regions along the sides of the openings (2), (3), in contact with the objects to be dispensed, may have sections or protuberances made of elastic materials so as to enhance the function of blocking the objects in the opening by elastically compressing said objects. The contact regions made of elastic materials along the sides of the elongate openings (2) may especially be discrete excrescences (7) such as those shown in FIGS. 1 to 3. The elastic contact regions along the sides of the openings may also be positioned over all or part of the length of the elongate opening, on just one side or preferably on both sides.

The regions made of elastic materials may be formed from at least one thermoplastic elastomer of natural or synthetic origin. The elastomer(s) may be preferably chosen from the group consisting of: elastomers of the natural rubber or synthetic rubber type, in particular mono-olefin rubbers such as, for example, isobutylene/isoprene, ethylene/vinyl acetate (EVA), ethylene-propylene (EPR), ethylene-propylene-diene monomer (EPDM) and ethylene/acrylic ester (EMA-EEA) polymers; fluoropolymers; diolefin rubbers, such as for example polybutadiene and butadiene-styrene (SBR) copolymers; rubbers based on condensation products such as, for example, polyester and polyurethane thermoplastic rubbers, silicones, styrene rubbers, such as styrene-butadiene-styrene (SBS) and styrene-isoprene-styrene (SIS) rubbers, and the like, used individually or in a blend.

The dispensing device (1) preferably has the shape of a disk as shown in the figures, but it may have many different shapes so as to fit various types of containers; for example, it may have an oval or square shape or it may have a hemispherical shape.

Guide surfaces (6), for guiding objects (13) to be dispensed, may also be positioned over part or all of the edges of the openings (2, 3), on the front face side, that is to say that side of the dispensing device (1) that is facing the stock of objects (13) to be dispensed. These guide surfaces (6) are preferably positioned on each edge, on either side of the elongate openings (2), and are oriented on the same side as the objects (13) to be dispensed, these objects being stored in the container (4).

Figure 4:
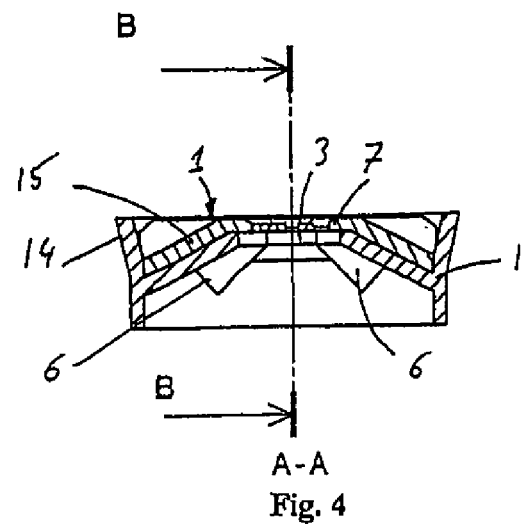
FIG. 4 shows a view in cross section on the axis A-A of the dispensing device.
Figure 5:
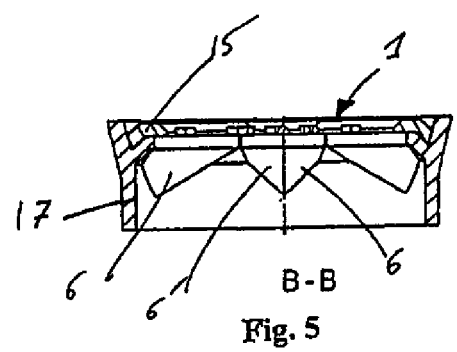
FIG. 5 shows a view in cross section on the axis B-B of the dispensing device.

The guide surfaces (6) are preferably planes inclined to the opening (2) so as to form a kind of hopper for collecting the objects to be dispensed, the outlet of said hopper forming the elongate opening (2). The angle of inclination of the guide surfaces (6) to the plane passing through the two sides of the opening (2) is generally between 20° and 60°, and preferably 45°. The guide surfaces (6, 6') of two neighboring and consecutive elongate openings (2, 2') (shown in FIGS. 3 to 5) form, in general, a dihedron having a sharp edge (15) for orienting the objects to be dispensed toward one or other of the neighboring openings (2, 2').

The guide surfaces (6) positioned on each side of the elongate openings (2) are preferably plane, but there may be surfaces of curvilinear cross section, in the form of recesses or raised features, or they may have any other shape fulfilling the function of guiding the objects toward said elongate openings.

To promote the guiding function, the guide surfaces are preferably made of rigid materials, which allow easy sliding of the objects to be dispensed.

The dispensing device (1) is preferably made of rigid polymer material by injection molding and includes the important functional aspects of the invention, namely:
the elongate openings (2);
the main dispensing opening (3);
the guide surfaces (6) oriented on the same side as the objects (13) to be dispensed and generally placed on either side of each of the elongate openings; and
if necessary, the elements for assembling the dispensing device (1) on the container (4).

The desirable polymer materials for producing the dispensing device, and more particularly the guide surfaces, are generally, but not exclusively, chosen from the group of materials composed of thermoplastic polymers, comprising in particular: polyolefins, such as polyethylenes, polypropylenes, ethylene/propylene copolymers and blends thereof; polyamides (PA); polystyrenes (PS); acrylonitrile-butadiene-styrene (ABS) copolymers and styrene-acrylonitrile (SAN) copolymers; polymethyl methacrylates (PMMA); polyethylene terephthalates (PET); polyvinyl chlorides; and polycarbonates.

The portion or portions (15) of the dispensing device that are made of elastic material(s) are generally molded over that part (17) of the dispensing device which is made of rigid material, the rigid part (17) generally constituting the main structure of the dispensing device (1). The elastic material is preferably fitted in the form of a layer (15) in which the resilient rims are formed, these being placed around the perimeter of the elongate openings (2) and/or of the main dispensing opening (3).

Figure 6:
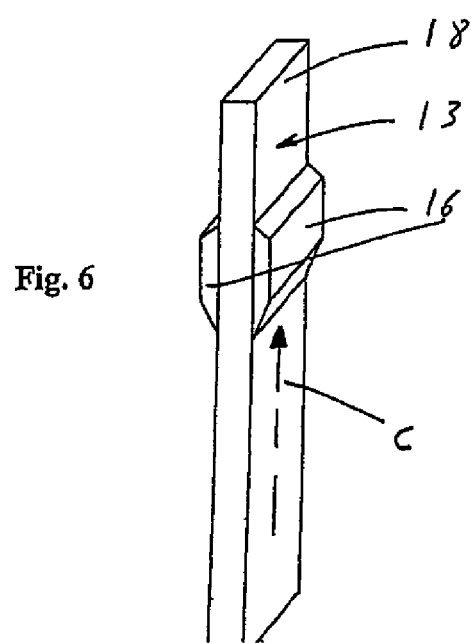
FIG. 6 shows a perspective view of a dispensed object.

FIG. 6 shows an oblong object (13), of generally plane parallelepipedal type, to be dispensed by the dispensing device (1).

The generally plane oblong objects are substantially identical to one another and have the shape of parallelepipedal strips or stems of elliptical cross section, polygonal cross section or circular cross section.

It has been found that the quality of the individual dispensing of objects can be improved by using parallelepipedal strips that have a slight protrusion (16) on at least one of the two plane faces of the object (13).

It has also been found that this protrusion must preferably be away from that end of the object which has to be inserted first into the main dispensing opening (3), so that the object (13) partially inserted into an elongate opening (2) is stopped in the elongate opening (2) and can normally exit only via the main dispensing opening (3). The protrusion (16) on the object (13) is generally positioned in the front third of the object to be dispensed, on the side closest to the dispensing device (1). This side is indicated by the arrow "C", which denotes the direction in which the object is dispensed.

It has also been found that this excrescence must preferably be away from that end of the object which has to be inserted first into the main dispensing opening (3), so that the object (13) partially inserted into an elongate opening (2) is stopped in the elongate opening (2) and can normally exit only via the main dispensing opening (3). The excrescence (16) on the object (13) is generally positioned in the front third of the object to be dispensed, on the side closest to the dispensing device (1). This side is indicated by the arrow "C", which denotes the direction in which the object is dispensed.

To improve the quality with which the objects are dispensed, it is preferable to orient these objects in a single direction (the direction of the arrow "C") so as to promote relatively uniform behavior of these objects during the dispensing operation. To do this, the stock of objects to be dispensed is generally placed in a container (4), the internal dimensions of which make it possible to maintain the relative orientation of the objects (13) with respect to the dispensing device (1).

The main function of the container (4) is to preserve the stock of objects to be dispensed so as to be protected from any external disturbance, which may be moisture, dust, mechanical degradation, such as shocks, or the like.

To do this, the container (4) is generally made of moisture-impermeable rigid polymer materials. Such materials may be chosen from the group formed by thermoplastic polymer materials comprising, in particular: polyolefins, such as polyethylenes, polypropylenes, ethylene/propylene copolymers and blends thereof; polyamides; polystyrenes (PS); acrylonitrile-butadiene-styrene (ABS) copolymers and styrene-acrylonitrile (SAN) copolymers; polymethyl methacrylates (PMMA); polyethylene terephtalates (PET); polyvinyl chlorides; and polycarbonates.

As mentioned above, and as shown in FIG. 1, the dispensing device (1) is generally fitted inside the container (4) that contains the objects (13) to be dispensed, forming an assembly for storing oblong objects and for dispensing them one by one. Such a method of assembly is preferred as it allows the dispensing device (1) to be produced independently of the containers (4), thus permitting interchangeability of the dispensing device on several types of container, and facilitating the operations of filling and refilling the container with objects to be dispensed.

Several ways of assembling the container (4) and the dispensing device (1) may be used. For example, it is possible to assemble them by screwing, bonding, snap-fastening or force-fitting the dispensing device (1) into the container (4). In the case of force-fitting assembly, said container is provided with a stop in order to lock the dispensing device (1) in position. Conical force-fitting is generally preferred as it not only positions the device relative to the container but also mechanically blocks the assembled parts. For example, the dispensing device shown in FIGS. 4 and 5 has a circular shape with a conical external surface portion (18) intended to bear on a complementary conical internal surface of the container (4). The dispensing device (1) is assembled with the container (4) so as to position the dispensing device near the opening of the container (4), thus leaving a large space free for storing the objects (13) to be dispensed.

According to the invention, and to fulfill the function of protecting the objects to be dispensed from moisture, it is also possible to provide the container (4) with a removable stopper (8), generally attached to the container via a hinge (9) the axis of rotation of which is approximately perpendicular to the main axis of the container (4). The stopper (8) may also be positioned on the container by any other conventional means of attachment, such as by using clips, by screwing the stopper onto the container, or by interlocking assembly.

Another particular way of protecting the objects from moisture may also be provided by the presence of absorbent or desiccant elements made from desiccating compositions formed from blends of thermoplastic polymers and/or copolymers and/or elastomers, by themselves or as a blend and from desiccants. These desiccating elements may be in the form of inserts, layers of materials molded onto the internal surface of the container (4) or incorporated into the material that forms the walls of the container, and/or inserted into the stopper (8) that closes off the container, and/or forming the stopper.

The desiccating elements may also form the constituent materials of the walls of the container (4) and/or of the stopper (8). As regards the desiccating compositions formed from blends of thermoplastic polymers and/or copolymers and of desiccants, the polymers and/or copolymers employed are chosen from those used for producing the device and the container, by themselves or as a blend, optionally combined with at least one elastomer used for producing the contact regions of the elongate openings (2).

The desiccant is generally chosen from the following types of material.

A first type of desiccant comprises chemical components that can be combined with water to form hydrates. Such desiccants may be:

anhydrous salts, which tend to capture water and moisture, forming hydrated salts;

anhydrous oxides that react with water or water vapor (atmospheric moisture) to form new hydrated compounds such as, for example, calcium oxide, magnesium oxide or the like.

Another type of desiccant has the capacity of absorbing moisture by capillary effect, due to the morphology of the material. Such materials are mainly silicas, in particular silica gels, clays, such as montmorillonite, molecular sieves, starch, and certain synthetic materials, such as polybutadienes and polysiloxanes The stopper (8) is preferably provided with a sealing groove (11) into which a sealing lip (10) of the container (4)

will be positioned, so as to seal the assembly when the container (4) is closed off by the stopper (8).

The dispensing device (1) described above has the important function of conveying the objects (13) to be dispensed toward the main dispensing opening (3). This conveying operation takes place in various steps:

firstly, the user inverts or shakes the dispensing device so that the object to be dispensed, undergoing an inertial movement, come into mechanical contact with the dispensing device lying beneath the objects to be dispensed;

in general, the objects undergo relatively random motions and lie in many different positions. The presence of inclined guide surfaces (6) on the edges of an elongate opening, on the same side as the stock of objects to be dispensed, allows some of these objects to be positioned and aligned with respect to the elongate opening (2);

the objects (13) to be dispensed, thus positioned and aligned along the elongate openings (2), have a tendency to slide under the effect of their inertia. The sliding generally takes place along the elongate opening (2) toward the main dispensing opening (3);

if no object to be dispensed is engaged in the main dispensing opening (3), then one of the objects guided along one of the elongate openings will be positioned and engaged in the main dispensing opening (3);

the object to be dispensed, thus positioned, partly blocks off the main dispensing opening, thus preventing another object to pass through it;

while it is being dispensed, the object remains generally positioned and blocked in the main dispensing opening (3), this blocking being preferably accentuated by the presence of resilient regions (7) placed around the perimeter of the main dispensing opening (3) and creating friction, which progressively slows down and then stops the object in the course of being dispensed; and the user can then easily collect the partially dispensed object accessible from the outside of the dispensing device. In general, the blocking of the object in the main dispensing opening is sufficient to immobilize the object in this opening and to allow the user to position or upturn the dispensing device so as to make it easier to grip the dispensed object.

The invention is not limited to the details of the embodiments and examples chosen to illustrate it. Modifications may be made without thereby departing from the scope of the invention.

The invention claimed is:

1. A device for dispensing oblong objects comprising:
a main dispensing opening for allowing the objects to be dispensed to pass therethrough one by one;
at least one other opening of elongate shape, one of whose sides opens into the main dispensing opening, the elongate opening having an opening width equal to or greater than a thickness of the object to be dispensed and wherein the elongate opening or openings comprise slots of substantially constant width; and
guide surfaces for guiding the objects to be dispensed, said surfaces lying along front sides of the elongate openings and facing the objects to be dispensed, so as to collect and guide said objects to be dispensed toward at least one of the elongate openings.

2. The device as claimed in claim 1, comprising at least two elongate openings arranged radially with respect to an axis of the main dispensing opening.

3. The device as claimed in claim 1, wherein the elongate opening or openings have the shape of slots.

4. The device as claimed in claim 3, wherein the slot-shaped elongate opening or openings have at least one of their sides curved, or two symmetrically curved sides, the curved sides forming a restriction.

5. The device as claimed in claim 1, wherein the elongate openings have a length at least equal to twice the width of the objects to be dispensed.

6. The device as claimed in claim 1, wherein the main dispensing opening is a circular opening, the diameter of which approximates a minimum width of the objects to be dispensed.

7. The device as claimed in claim 1, wherein the rim of at least one of the openings includes at least one portion made of elastic material, said portion being intended to allow an object dispensed to be held in the opening by being lightly gripped therein.

8. The device as claimed in claim 7, wherein the elastic material is selected from the group consisting of natural rubbers, mono-olefin rubbers, isobutylene/isoprene, ethylene/vinyl acetate (EVA), ethylene propylene (EPR), ethylene-propylene-diene monomer (EPDM), ethylene/acrylic ester (EMA-EEA) polymers; fluoropolymers; diolefin rubbers, polybutadienes, butadiene-styrene (SBR) copolymers, rubbers based on condensation products, polyester and polyurethane thermoplastic rubbers, silicones, styrene rubbers, styrene-butadiene-styrene (SBS) and styrene-isoprene-styrene (SIS) rubbers.

9. The device as claimed in claim 1, comprising the form of a disk.

10. The device as claimed in claim 1, wherein the guide surfaces for guiding the objects to be dispensed are made of rigid material, allowing sliding of the objects to be dispensed.

11. The device as claimed in claim 1, wherein the rigid material constituting the guide surface is at least selected from the group consisting of polyethylenes, polypropylenes, ethylene/propylene copolymers and blends thereof; polyamides; polystyrenes (PS); acrylonitrile butadiene-styrene (ABS) copolymers and styrene-acrylonitrile (SAN) copolymers; polymethyl methacrylates (PMMA); polyethylene terephthalates (PET); polyvinyl chlorides; and polycarbonates.

12. The device as claimed in claim 1, wherein the dispensed objects are identical to one another and are in the form of parallelepipedal strips or stems of elliptical, polygonal or circular cross section.

13. A container for containing objects to be dispensed and having at least one opening into which the dispensing device of claim 1 is mounted.

14. The object-dispensing container as claimed in claim 13, wherein the dispensing device is assembled inside the container.

15. The dispensing container as claimed in claim 13, wherein the container is closed off in a sealed manner by a removable stopper.

16. The container as claimed in claim 15, wherein the stopper is articulated to the container via a hinge, an axis of which is approximately perpendicular to an axis of the container.

17. The container as claimed in claim 13 formed from at least one thermoplastic polymer material selected from the group consisting of polyethylenes, polypropylenes, ethylene/propylene copolymers and blends thereof; polyamides; polystyrenes (PS); acrylonitrile-butadiene=styrene (ABS) copolymers and styrene-acrylonitrile (SAN) copolymers; polymethyl methacrylates (PMMA); polyethylene terephthalates (PET); polyvinyl chlorides; and polycarbonates.

18. The container as claimed in claim 13, including at least one desiccating element.

19. The container as claimed in claim 18, wherein the desiccating element comprises desiccating layers molded onto an internal surface of the container and/or of the stopper.

20. The container as claimed in claim 18, wherein the desiccating element constitutes walls of the container and/or of the stopper.

21. The container as claimed in claim 18, wherein the desiccating element comprises (i) desiccating compositions formed from blends of thermoplastic polymers and/or copolymers and (ii) mineral desiccants.

22. The container as claimed in claim 21, wherein the thermoplastic polymers and/or copolymers forming the desiccating element are selected from those forming said container, taken by themselves or as a blend, optionally combined with at least one elastomer used for producing elastic contact regions of the elongate openings.

23. The container as claimed in claim 18, wherein the desiccants used in the composition of the desiccating elements are selected from the group consisting of anhydrous metal salts, metal oxides that can react with water vapor, silica gels, molecular sieves, starch, montmorillonite, polybutadienes and polysiloxanes.

24. A container that is assembled with a device defined by claim 1, wherein said container forms an assembly for the storage and dispensing of oblong objects.

25. A device of claim 1 wherein said objects are substantially polygonal, circular, or elliptical.

26. A device of claim 1 wherein the elongate opening further comprise resilient regions extending from the elongate opening to create friction on objects being dispensed.

27. A device for dispensing oblong objects comprising:
a main dispensing opening for allowing the objects to be dispensed to pass therethrough one by one;
at least one other opening of elongate shape, one of whose sides opens into the main dispensing opening, the elongate opening having an opening width equal to or greater than a thickness of the object to be dispensed and wherein the elongate opening or openings are slots whose width increases toward the main dispensing opening; and
guide surfaces for guiding the objects to be dispensed, said surfaces lying along front sides of the elongate openings and facing the objects to be dispensed, so as to collect and guide said objects to be dispensed toward at least one of the elongate openings.

* * * * *